United States Patent [19]

Connel

[11] 4,034,753
[45] July 12, 1977

[54] GAS ANESTHESIA MACHINE

[76] Inventor: Allan A. Connel, 14303 N. 60th St., Oak Park Heights, Stillwater, Minn. 55082

[21] Appl. No.: 617,989

[22] Filed: Sept. 29, 1975

[51] Int. Cl.² .................. A61M 16/00; A62B 7/02
[52] U.S. Cl. ............................ 128/188; 128/191 R
[58] Field of Search ............ 128/188, 186, 191 R, 128/192, 193, 202, 194; 261/71, 112, 104, 103, DIG. 65; 23/284

[56] References Cited

U.S. PATENT DOCUMENTS

| | | | |
|---|---|---|---|
| 1,061,539 | 5/1913 | Haertel | 128/202 |
| 1,903,301 | 4/1933 | Snowden et al. | 261/103 |
| 2,104,988 | 1/1938 | Heidbrink | 128/191 R X |
| 2,141,794 | 12/1938 | King | 128/188 |
| 2,241,535 | 5/1941 | Boothby et al. | 128/202 X |
| 3,123,071 | 3/1964 | Felts | 128/188 |
| 3,221,737 | 12/1965 | Felts | 128/188 |
| 3,620,213 | 11/1971 | Savoie, Jr. | 128/142 |
| 3,794,027 | 2/1974 | Johnson | 128/188 |

FOREIGN PATENT DOCUMENTS

| | | | |
|---|---|---|---|
| 604,587 | 5/1926 | France | 128/202 |
| 1,133,728 | 4/1957 | France | 128/202 |
| 548,092 | 1/1923 | France | 128/188 |
| 36,012 | 10/1922 | Norway | 128/191 |
| 221,323 | 9/1967 | Sweden | 128/188 |

Primary Examiner—J. Reed Fisher

[57] ABSTRACT

An anesthetic machine is provided with a means of supplying oxygen with or without an anesthetic which is supplied in measured quantities to the patient, whether a human or other animal. The anesthesia is provided in accurate dosage to the human or animal.

4 Claims, 4 Drawing Figures

GAS ANESTHESIA MACHINE

This invention relates to an improvement in an anesthetic machine in which the amount of anesthetic fluid which is used is definitely metered and combined with another fluid such as oxygen to provide the desired result.

BACKGROUND OF THE INVENTION

For about 100 years, the use of gases for anesthetizing patients so that they will feel no pain during an operation or the like have been used. The present invention resides in the provision of an apparatus which will definitely proportion the amount of anesthetizing gases which are produced so that the patient will be anesthetized to the desired extent, and will not be subject to too much anesthetic while still producing the desired effect.

In the past the patient was anesthetized by inhaling an anesthetizing gas from a mask or other such means placed over the inhalation orifices (nose, mouth) of the person or animal. While the amount of such gas may be inhaled by a normal body of the person is known to the persons applying the anesthesia, the use of such a gas on animals of different types varies with the size of the animal.

Anesthesia machines of the types presently employed for the most part utilize a closed vessel containing various amounts of the anesthetic liquid at all times. The liquid is vaporized or changed to the gaseous state by a flow of oxygen, air, or both in combination passing over a pervious material soaked in the anesthetic liquid, or by bubbling through the fluid freely, or by gases passing over the surface of the fluids.

In the present device, there is no free residual fluid present at any time. The volatile anesthetic is vaporized or evaporated more or less instantly as it contacts the evaporating surfaces, over which it is directed.

SUMMARY OF THE DISCLOSURE

A further feature of the present invention resides in a closed or circle system in which the air exhaled by the patient passes through an absorption chamber including a material capable of absorbing carbon dioxide. Rather than to rely on the inhalation and exhalation of the patient, a motored fan is provided in the circuit to direct the air to the breathing bag either through the evaporator chamber or through a by-pass, and back through the fan to the patient.

The use of a constant mechanically maintained flow of circulating gases offers the following advantages:

1. Gases flow continuously through the carbon dioxide absorber thus increasing the efficiency of carbon dioxide removal.
2. Constant induced circulation means that the patient does not operate the machine by his own inspiratory and expiratory efforts.
3. The constant flow through the evaporator (instead of only when the patient breathes) means vaporization rate is constant if there is fluid anesthetic being admitted to the evaporative surfaces.

An important feature of the present invention lies in the vaporizer itself which has been defined as a "dry evaporator". The advantages are:

1. The capabilities to vaporize all commonly employed volatile anesthetic agents, singly, in combination, or alternately if desired.
2. The negative loss of latent heat during operation.
3. The capability of achieving extreme precision in delivering desired levels of anesthetic gas or gases into the carrier gases (vapor concentration or percent).
4. Economy; no free fluid is lost through evaporization when not in use.
5. Simplicity of design with lower cost of production.
6. Ease and simplicity of operation.
7. The amount of volatile anesthetic used or consumed for each individual use period is readily and accurately determined, both during the operative procedure, and at termination.
8. Safety devices are provided including a pop-off valve, oxygen quick flush arrangement, and a safety valve to allow exhaled gases from the carbon dioxide absorber to by-pass the evaporator.

The purpose of this invention is to provide an apparatus which will provide a predetermined amount of anesthetic to an animal or human at a predetermined rate. For example, if a small animal such as a household pet is anesthetized, only a relatively small amount of anesthetic is required to be supplied at a relatively low flow rate; while for a large animal a much greater amount of anesthetic is supplied, and at a relatively greater rate of flow. The present device is capable of accurately measuring the amount of anesthetic supplied, and accurately measuring the rate of flow of the anesthetic being supplied.

In many instances, the exhaled air, after passing through a carbon dioxide absorbing chamber, is mixed with oxygen, nitrous oxide, or air. When an anesthetic is to be combined with the exhaled gases and oxygen, the oxygen and exhaled air from which the carbon dioxide has been removed is directed through a dry evaporating chamber. This chamber may comprise a generally rectangular housing including inclined baffles secured to opposite walls of the housing, the baffles being in vertically spaced relation. Alternate baffles are secured to one wall, and the remaining baffles incline from the opposite wall of the housing. The arrangement is such that liquid anesthetic may flow down the uppermost baffle over which the oxygen and exhaled gases are directed, the volatile anesthetic being picked up by the gases. The unvolatilized anesthetic liquid flows over the edge of the first baffle to flow down the surface of the second baffle where more of it is volatilized and entrained in the air and oxygen. This continues as the gases passes over the third baffle, and usually the volatilization is complete by this time. Any unvolatilized liquid may be volatilized while the gases flow over the fourth baffle, and no liquid anesthetic ever reaches the bottom of the dry absorption chamber.

In general, the device includes an inlet duct into which the air exhaled by the patient is directed, and an absorbent chamber of soda lime or similar material capable of absorbing carbon dioxide is connected to the inlet duct, to remove the carbon dioxide from the exhaled air. From there, the gases may be combined with oxygen and directed into the top of the dry evaporator chamber in which the gases pick up volatilized liquid anesthetic. The gases then flow into a breathing bag. A motor driven fan in the circuit drives the gases from the breathing bag to an inhalation duct connected to the breathing mask or endotracheal tube. A by-pass is provided from the bottom of the absorbent chamber to the inhalation duct so that the carbon dioxide free air and oxygen may flow directly to the inhalation duct, by-passing the dry evaporator. This is controlled by an operator actuated valve.

A further feature of the present invention resides in the provision of metering vials, which are transparent and exposed to the operator so that the vials may be filled to the desired extent to provide the proper amount of the anesthetic to be used. When filled to the desired level according to volume desired, the outlet of these vials may be regulated to supply the liquid anesthetic in the proper proportion. The drip meter, in turn supplies the proper proportion of liquid anesthetic to the dry evaporator chamber in which the oxygen and other circulating gases picks up a larger or smaller amount of the volatile liquid in the form of gas which is then directed to the breathing bag and drawn by a suitable motor driven pump to the inhalation duct of the apparatus. The visible flow meters may show the proportion of oxygen and the anesthetic material which is being directed through the dry evaporator chamber.

A further feature of the present invention resides in the provision of a control panel including a series of calibrated transparent cylindrical chambers by means of which the operator may visually note the amount of oxygen and anesthetizing liquid being used, and including a metering valve which is desired to proportion the amount of fluid which enters the drip box. In preferred form, the drip meter or drip box is likewise transparent so that the amount of fluid being admitted therein may be readily seen.

The novel feature of the present invention will be more clearly and fully set forth in the following specification and claims.

DESCRIPTION OF THE PREFERRED EMBODIMENTS

Figures 1, 2, 4:
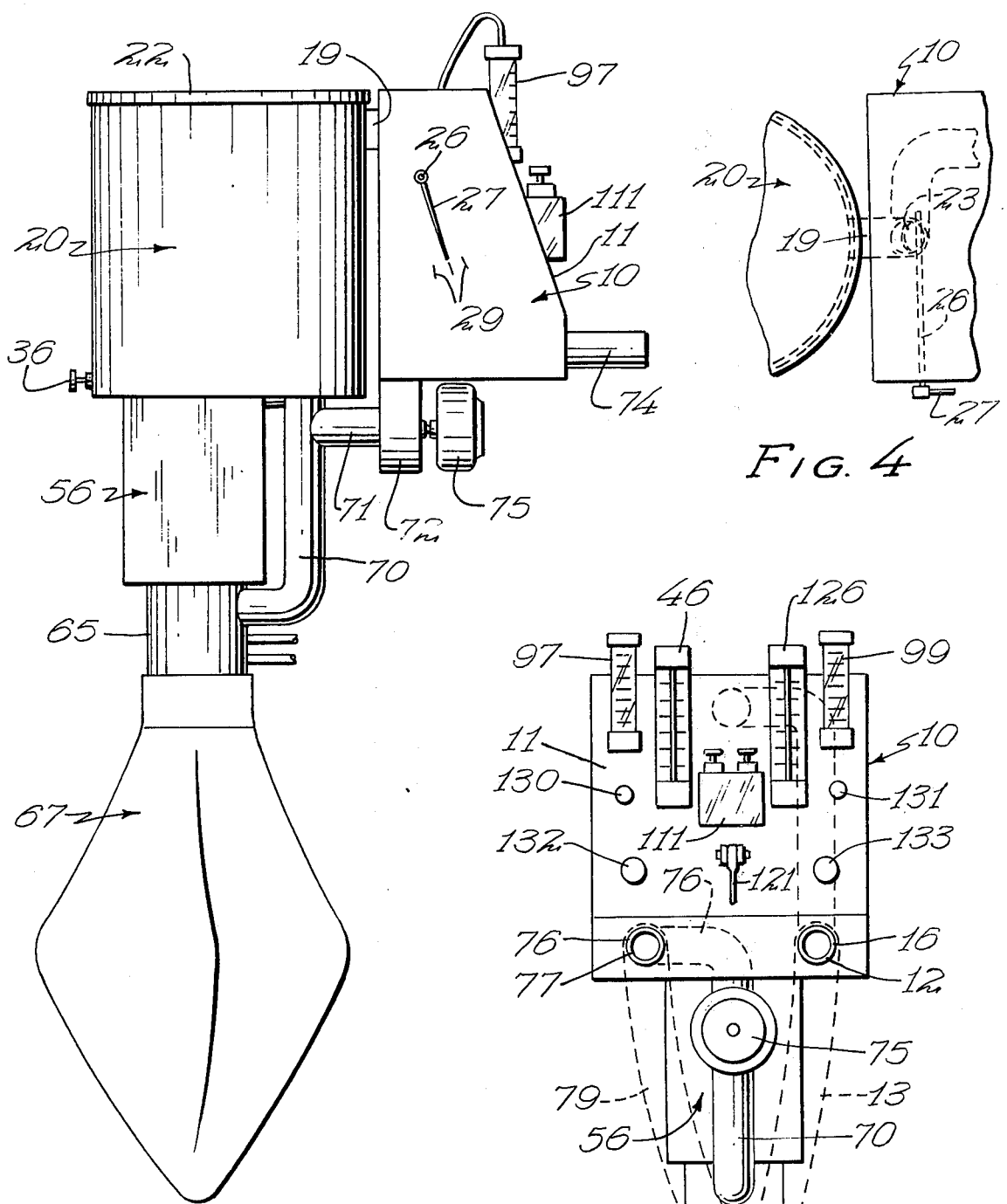
FIG. 1 is a diagrammatic side view of the machine.
FIG. 2 is a front view of the control panel.
FIG. 4 is a top plan view of a portion of the absorption chamber and control box showing an indicator to be used in conjunction with the flap valve and to indicate whether the flap valve is in open or closed position.

As indicated in the drawings, the control box 10 includes a front panel 11 provided with an exhalation port 12 (see FIG. 2). This port is connected by a flexible hose 13 terminating in a Y connection 14 connected by a tubular member 15 to the mask or the like into which the air of the patient is exhaled. The exhalation port 12 is connected by a tubular member 16 (see FIG. 3) which extends through the control box and extends upwardly as indicated at 17 within the control box, the upper extremity 19 of which extends into the upper end of an absorption chamber 20 above the level of the carbon dioxide absorbent material such as soda lime 21. The chamber 20 is provided with a removal cover 22 to permit the soda lime or other carbon dioxide absorbing material to be inserted.

A flap valve 23 is provided in the tubular connection which normally seats against the valve seat 25 when no air is entering the exhalation port 12. The flap valve 23 is mounted upon a shaft 26 which supports a pointer 27 which is directed toward indicating marks 29 which provide an indication of the position of the flap valve 23.

Figure 3:
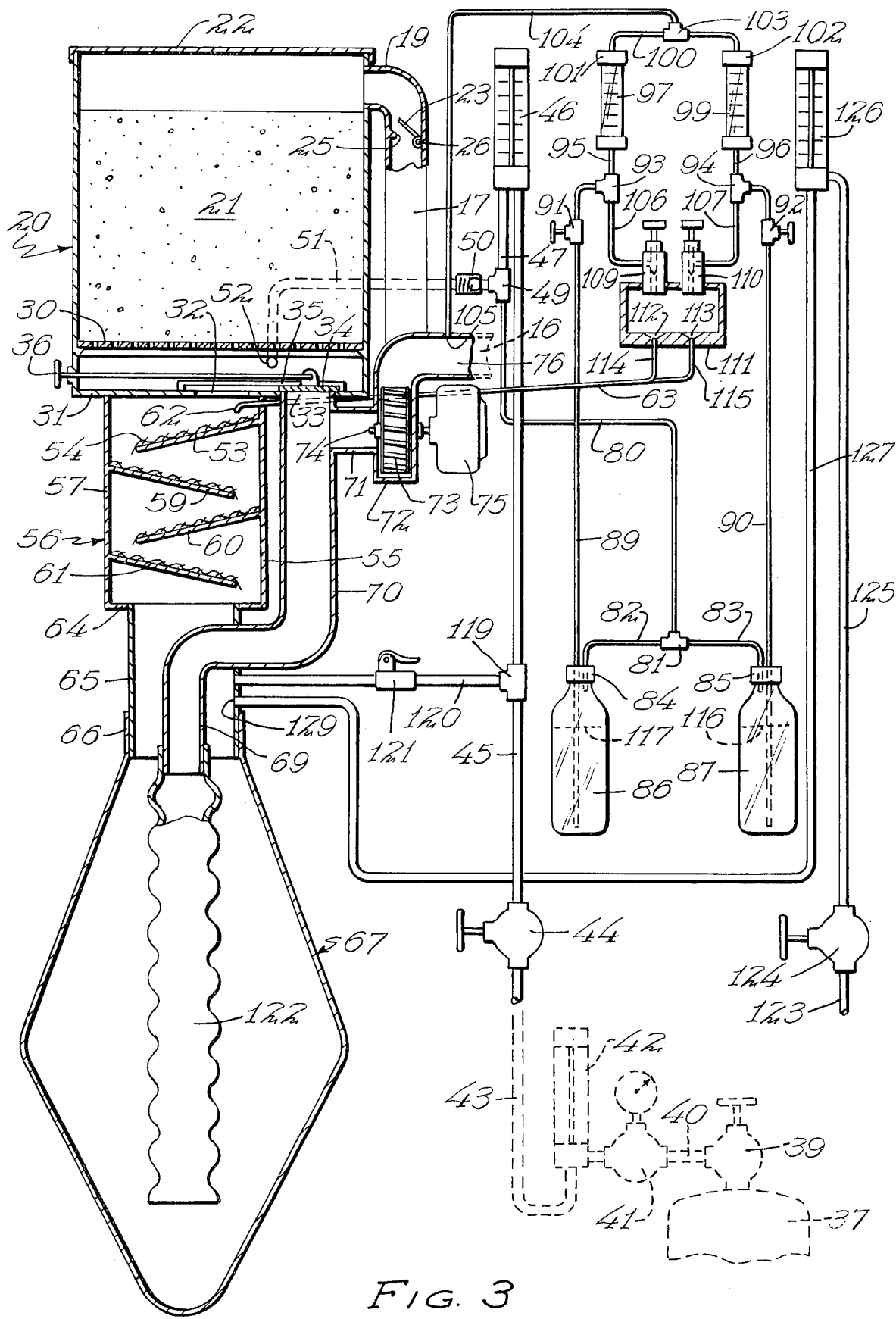
FIG. 3 is a diagrammatic view to show the various circuiting.

The absorption chamber 20 includes a perforated plate or screen 30 which supports the body of carbon dioxide absorbing material 21. The bottom panel 31 of the chamber 20 is spaced below the screen 30 and is provided with a first aperture 32 and a second aperture 33. A slidable valve or closure plate 34 is supported for sliding movement upon the bottom panel 31 by suitable guides 35. A push-pull rod 36 is connected to the top of the member 34, and may be used to close either of the apertures 32 or 33. In FIG. 3 of the drawings, the valve plate 34 is in position to close the orifice 33, leaving the orifice 32 open.

Oxygen is supplied from a supply tank such as 37 through a main valve 39 and through a conduit 40 and through a pressure reducing valve 41 and a flow meter 42 to a supply line 43. This tank and the valves described are shown in dotted outline, as another oxygen supply may be provided which is controlled with the valve 44. The valve 44 is connected by a pipe 34 to the flow meter 46, and leaves the flow meter through an outlet pipe 47.

The pipe 47 extends through a T connection 49 through the back pressure valve 50 and passage 51 to terminate at 52 in the area beneath the screen 30 and above the bottom panel 31 of the absorption chamber 20. When valve 34 is in the position illustrated in the drawings, the exhaled gases, together with the oxygen passes over an inclined baffle 53 having a flow resistant material such as fiberglass cloth 54 on its upper surface. The baffle 53 is connected to one wall 55 of the dry evaporator chamber 56 and terminates short of the opposite wall 57 of the chamber 56. Liquid passing over the end of the baffle 53 will drop onto an oppositely inclined baffle 59 similarly covered with fiberglass cloth or the like, and secured to the wall 57 of the chamber 56. A similar third baffle 60 parallel to the first baffle 53 collects any moisture flowing past the end of the baffle 59, and a fourth baffle 61 similarly constructed to the other baffles is mounted on the wall 57 of the chamber 56 in parallel relation to the baffle 59. Liquid anesthetic from a supply to be described flows from the end 62 of a tubular connection 63 leading to an anesthetic supply which will be described. This liquid anesthetic flows in a zig-zag direction through the dry evaporator chamber 56 and the exhaled gases, mixed with oxygen, flow through the orifice 32 and over the various baffles, picking up the volatile anesthetic liquid and combining it in gaseous state.

The bottom wall 64 of the chamber 56 is apertured to communicate with a large diameter tube 65, the lower end of which is encircled by the sleeve like upper end 66 of the breathing bag 67. A tubular member 69 extends upwardly axially of the much larger diameter tubular member 65 and is curved to extend through the wall thereof and then upwardly as indicated at 70 to terminate flush with upper surface of the bottom panel 31 of the absorption chamber 20. A laterally extending tubular member 71 communicates with the interior of the tubular member 70, and connects it with the fan housing 72. A fan 73 is supported on a shaft 74 driven by a motor 75. The outlet of the fan 73 forces the gases through a tubular duct 76 connunicating with the inhalation port 77 which extends forwardly of the front wall 11 of the control box 10 for attachment with a flexible hose 79 connected to the second branch of the Y connection 14 having its stem connected by the tube 15 which may be described as an endotracheal tube. This is best illustrated in FIG. 2 of the drawings.

As has been described, oxygen from a source of supply may flow through the tubular connection 45 to the flow meter 46 which measures the flow of oxygen passing through the flow meter and into the outlet 47. This tubular outlet 47 is connected by the T connection 49 and the tube 51 to the outlet 52 terminating just beneath the screen 30 in the absorption chamber 20. The oxygen may also flow through the tube 80 to a T connector 81 the ends of which are connected by right angular tubes 82 and 83 which are inserted through the apertured stoppers 84 and 85 of the fluid anesthetic bottles 86 and 87. The purpose of this arrangement is to supply oxygen under relatively low pressure above the liquid anesthetic bottles 86 and 87 to force the liquid from the bottles. The anesthetic may be any liquid anesthetic agent or drug such as methoxyflurane, halothane, forane, and ethrane. Obviously, any volatile liquid anesthetic may be used and those listed are merely examples of fluid which are commonly used. Outlet tubes 89 and 90 extend through the apertured stoppers 84 and 85 to a position close to the bottoms of the bottles 86 and 87. The tubular members 89 and 90 include push button valves 91 and 92 which are of the type which automatically close when the force of operating the push buttons is released. The tubes 89 and 90 are connected by T connectors 93 and 94 to tubes 95 and 96 extending into the lower ends of metering vials 97 and 99. A vent pipe 100 extends through the upper c closures 101 and 102 of the metering vials 97 and 99 and are connected by a T connector 103 to a tubular connector 104 which communicates with the inhalation tube 76 and 105. The other ends of the T connectors 93 and 94 are connected by the tubes 106 and 107 to metering valves 109 and 110 extending into a drip meter chamber 111. The under surface of the drip meter chamber 111 is apertured as indicated at 112 and 113 which are in communication with tubes 114 and 115 which communicate with the tubular member 63 leading downwardly and terminating at 62 in the dry evaporator chamber 56 as has been described. One of the liquid anesthetic supply bottles such as 87 is designed to accommodate a high volatility fluid anesthetic such as 116. When the push button valve 92 is opened, the oxygen pressure above the fluid in the bottle forces the fluid up through the tube 90 and the valve 92 to the T connector 94 and upwardly through the tube 96 to the metering vial 99. The amount of liquid flowing through the pipe 107 to the control valve 110 is minimized by the fact that the control valve 110 is normally set to dispense the anesthetic a drop at a time, the drops being dispensed at intervals. The valve 92 is manually opened until a predetermined amount of a liquid anesthesia enters the vial 99 as determined by the calibrations on the surface of the transparent vial. The air within the vial is displaced through the tube 100, the T connector 103 and the tube 104 leading to the inhalation duct 76 and 105.

In a similar manner the relatively low volatility anesthesia 117 in the bottle 86 may be forced upwardly through the tube 89 when the valve 91 is manually opened, filling the vial with the desired amount of liquid anesthetic which is dispensed a drop at a time through the tube 106 and metering valve 109. Thus, the lower volatility liquid anesthesia may be directed through the tube 63 and the outlet 62 onto the upper surface of the upper baffle 53.

A T connector 119 in the oxygen supply pipe 45 is connected by the tubular connector 120 to the tubular member 65 so that oxygen in the full force of that in the tube 45 is directed into the tubular member 65 when the hand operated valve 121 is opened. This valve is opened to provide a quick flush of the gases within the breathing bag 67 or when a greater amount of oxygen is required at the inhalation port 77. The fact that the breathing bag is suspended downwardly from the tube 65 provides a great opportunity for the gases within the bag to be thoroughly mixed before being dispensed through the perforated duct 122. This duct 122 is suspended from the lower end of the tubular member 69.

Some doctors using the apparatus in anesthetizing animals or humans prefer to use a material such as nitrous oxide instead of, or in combination with, a various liquid anesthetic. Other doctors prefer air to be used in combination with anesthetics of merely to supply air to the patient. At the right hand side of the FIG. 3, a pipe 123 is provided leading to a supply of pressurized nitrous oxide or other gaseous anesthetic material. The flow through the pipe 123 from the pressurized supply is controlled by a valve 124 which is connected by the tubular connection 125 to the flow meter 126 which measures the fluid being dispensed. The flow meter 126 indicates the flow through the tubular connection 127 which terminates at 129 in communication with the interior of the tubular connection 65 leading to the breathing bag 67. This nitrous oxide may be drawn from the breathing bag 67 through the porous duct 122 and outlet tube 69 and drawn by the fan 73 to the inhalation outlet 77. Thus, the gas being used, and the liquid anesthetics which are used may depend upon the wishes of the operator. Accordingly, the apparatus is extremely versatile, and various arrangements may be used depending upon the operating doctor.

The drawings and particular diagrammatic view does not necessarily show the arrangement of parts to be actually used. For example, the motor 75 and fan 73 may be mounted upon the top panel 22 of the absorption chamber to force the gases through the system. The transparent metering vials 97 and 99 as well as the flow meters 46 and 126 may be mounted on the control box so as to be readily visible to the operator. The drip meter chamber is also preferably formed of transparent material so that the flow from the metering valves 109 and 110 may be readily visible. The push buttons controlling the metering valve may be actuated by push buttons such as 130 and 131 projecting through the front panel 11 of the control box 10. The oxygen supply valve 44 and the nitrous oxide control valve operated by turning needle valves such as indicated at 132 and 133. The quick flush valve 121 may also be supported on the ooperating panel as well as switches controlling the motor 75, panel lights and the like. Thus, the drawings show the fundamental idea of the invention rather than necessarily the detail construction thereof. It is the combination of elements which is believed novel rather than the particular construction thereof.

In accordance with the Patent Statutes, I have described the principles of construction and operation of my Gas Anesthesia Machine, and while I have endeavored to set forth the best embodiments, I desire to have it understood that obvious changes may be made within the scope of the following claims without departing from the spirit of my invention.

I claim:
1. An anesthesia device including:
   an exhalation duct, a carbon dioxide absorption chamber to which said duct is connected, a dry evaporator chamber connected to said absorption chamber for receiving gases therefrom, a breathing bag connected to said dry evaporator chamber to receive gases passing therethrough, an inhalation duct extending from the interior of said breathing bag, said dry evaporator chamber including a series of spaced inclined baffles over which volatile liquid anesthetic may flow first in one direction and then in the opposite direction, at least one pressurized volatile liquid anesthetic container, a metering vial connected thereto by a tubular duct, a manually operable normally closed valve in said tubular duct for supplying a predetermined amount of volatile liquid anesthetic to said metering vial, a drip chamber connected to said metering vial to receive the liquid anesthetic a drop at a time, and means connecting said drip chamber to the dry evaporator chamber above the uppermost of said baffles.

2. The structure of claim 1 and including a by-pass for said gases from said carbon dioxide absorption chamber to said inhalation duct, by-passing said dry evaporator chamber.

3. The structure of claim 1 and in which said vial and said drip chamber are formed of transparent material.

4. The structure of claim 1 and including a second supply of pressurized liquid anesthetic, a second metering vial connected to said second supply by a second tubular duct, a second manually operable normally closed valve in said second tubular duct, and means connecting said second metering vial to said drip chamber to deliver anesthetic from said second metering vial.

* * * * *